US011661444B2

(12) United States Patent
Montesino Segui et al.

(10) Patent No.: US 11,661,444 B2
(45) Date of Patent: May 30, 2023

(54) RECOMBINANT VACCINE AGAINST PROLIFERATIVE ENTEROPATHY IN ANIMALS

(71) Applicant: UNIVERSIDAD DE CONCEPCIÓN, Concepción (CL)

(72) Inventors: Raquel Montesino Segui, Concepción (CL); Jorge Toledo Alonso, Concepción (CL); Alvaro Ruiz Garrido, Concepción (CL); Oliberto Sanchez Ramos, Concepción (CL); Nicolas Gutierrez Mella, Concepción (CL); Omar Farnos Villar, Concepción (CL); Angela Hidalgo Gajardo, Concepción (CL); Eduardo Ramos Delgado, Concepción (CL); Marcelo Cortez San Martin, Concepción (CL)

(73) Assignee: UNIVERSIDAD DE CONCEPCIÓN, Concepción (CL)

( * ) Notice: Subject to any disclaimer, the term of this patent is extended or adjusted under 35 U.S.C. 154(b) by 416 days.

(21) Appl. No.: 16/643,147

(22) PCT Filed: Aug. 28, 2018

(86) PCT No.: PCT/CL2018/050073
§ 371 (c)(1),
(2) Date: Feb. 28, 2020

(87) PCT Pub. No.: WO2019/041056
PCT Pub. Date: Mar. 7, 2019

(65) Prior Publication Data
US 2021/0221855 A1 Jul. 22, 2021

(30) Foreign Application Priority Data
Aug. 30, 2017 (CL) .................................. 2196-2017

(51) Int. Cl.

| | |
|---|---|
| *C12Q 1/68* | (2018.01) |
| *C07K 14/195* | (2006.01) |
| *A61P 31/04* | (2006.01) |
| *A61K 38/21* | (2006.01) |
| *A61K 39/02* | (2006.01) |
| *A61K 39/39* | (2006.01) |
| *C12N 15/70* | (2006.01) |
| *A61K 39/00* | (2006.01) |

(52) U.S. Cl.
CPC .......... *C07K 14/195* (2013.01); *A61K 38/212* (2013.01); *A61K 39/105* (2013.01); *A61K 39/39* (2013.01); *A61P 31/04* (2018.01); *C12N 15/70* (2013.01); *A61K 2039/55522* (2013.01)

(58) Field of Classification Search
None
See application file for complete search history.

(56) References Cited

FOREIGN PATENT DOCUMENTS

| | | | |
|---|---|---|---|
| ES | 2266090 | T3 | 3/2007 |
| WO | 0238594 | A1 | 5/2002 |
| WO | 2006116763 | A2 | 11/2006 |
| WO | 2010048252 | A1 | 4/2010 |

OTHER PUBLICATIONS

Porin Family Protein [*Lawsonia intracellularis*], May 14, 2017 [retrieved Apr. 12, 2018], 1 pg., online URL: https://www.ncbi.nlm.nih.gov/protein/WP_011526924.1.

International Search Report and Written Opinion for related PCT App No. PCT/CL2018/050073 dated Dec. 11, 2018; English translation of ISR provided; 14 pgs.

*Primary Examiner* — Jennifer E Graser
(74) *Attorney, Agent, or Firm* — Procopio, Cory, Hargreaves & Savitch LLP

(57) ABSTRACT

The present invention relates to a recombinant vaccine against *Lawsonia intracellularis*, based on a recombinant synthetic chimeric variant of membrane proteins and invasins of said bacteria. In addition, the invention discloses synthetic nucleotide sequences encoding said protein variants, recombinant proteins as such, an expression cassette of said synthetic protein antigens, a transformed cell, and a method for producing said antigens, demonstrating the antigenicity and protective potential thereof against the pathogen *Lawsonia intracellularis*.

3 Claims, 5 Drawing Sheets

Specification includes a Sequence Listing.

RECOMBINANT VACCINE AGAINST PROLIFERATIVE ENTEROPATHY IN ANIMALS

TECHNICAL FIELD

The present invention relates to the technical field of veterinary pharmaceuticals, particularly, it is provided a recombinant vaccine against proliferative enteropathy in animals, caused by the *Lawsonia intracellularis* bacterium.

BACKGROUND OF THE INVENTION

There are several factors that limit pig production, the most important being diseases. Proliferative enteropathy (PE) is a pathology that affects the intestine of various mammals, mainly pigs, which affects the industry worldwide. This disease is characterized by thickening of the mucous membrane of the small intestine due to the proliferation of the intracellular bacterium *Lawsonia intracellularis*.

Pigs infected with said bacterium have symptoms such as weight loss, growth retardation, and hemorrhagic diarrhea, even leading to death. This results in significant economic losses along with the corresponding health risk for the pig industry in Chile and the world. Recent studies have analyzed the prevalence of the disease, indicating that it can reach between 60 and 100% of pigs in the United States and Europe (Machuca, M. A. et al. (2017). *Serological and histopathological survey of Lawsonia intracellularis infection in* 30 *argentinean swine herds. Brazilian Journal of Veterinary Pathology*, 2(1), 8-11).

Regarding the studies on the pathogenesis of *L. intracellularis*, the mechanism to induce enterocyte proliferation in infected animals is unknown, the virulence factors of *L. intracellularis* have not been characterized, and it is even suggested that the bacterium could modulate the host's immune response, decreasing the number of T and B lymphocytes in vivo (Gebhart, C. J., and Guedes, R. M. C. (2010). *Lawsonia intracellularis. Pathogenesis of bacterial infections in animals*, 3, 363-372).

Regarding the existing solutions disclosed in the prior art for the treatment against this disease in animals, the publication of Kroll, J. J. et al. (2004), *Evaluation of protective immunity in pigs following oral administration of an avirulent live vaccine of Lawsonia intracellularis. American journal of veterinary research*, 65(5), 559-565, describes an avirulent live vaccine of *L. intracellularis* for pigs. Said publication indicates that the immunogenic sites of the bacterium have not been fully explored, and that initial studies mention external membrane proteins and glycoproteins in general. Moreover, it emphasizes that the use of antigenic peptides alone does not produce a protective immune response in animals compared to the use of live avirulent bacteria as a whole.

In parallel, U.S. Pat. No. 9,636,389 describes a prophylactic method against *Lawsonia intracellularis* and another infectious agent, which involves the administration of a modified live strain of *L. intracellularis*. The recent publication of Riber, U. et al. (2015), *Vaccination of pigs with attenuated Lawsonia intracellularis induced acute phase protein responses and primed cell-mediated immunity without reduction in bacterial shedding after challenge, Vaccine*, 33(1), 156-162, indicates that when using the attenuated live vaccine of *Lawsonia intracellularis* (Enterisol® Ileitis, Boehringer Ingelheim) it was not possible to eliminate the bacterium from the body of treated pigs, further suggesting that protective vaccines that are able to effectively stimulate T lymphocytes should be developed. These solutions that use live bacteria represent a high risk, as they could reverse their virulence and make the treated animals sick, producing the unwanted opposite effect.

On the other hand, U.S. Pat. No. 9,463,231 discloses a pharmaceutical composition comprising a mixture of dead *L. intracellularis* bacteria, in combination with other pathogens antigens. Within the recombinant vaccines against *L. intracellularis*, various antigens have been disclosed, such as: endonucleases (application US20070212373), hemolysin (U.S. Pat. No. 7,029,683), flagellins (U.S. Pat. No. 8,025,884), and proteins that are located in the outer membrane of said bacterium (US20110200631).

Although several vaccine variants to control proliferative enteropathy in animals have been provided, few of them reach the market and have the required protective efficacy. Therefore, it is still necessary to obtain new properly functional vaccines for the livestock industry, in a way that allows the prevention and control of this disease.

BRIEF DESCRIPTION OF THE FIGURES

FIG. 1B corresponds to the T7 terminator; and FIG. 1C corresponds to the T7 Promoter/Lac Operator.

FIGS. 2A and 2B show the expression of the three antigens; and FIGS. 2C and 2D show purified antigens as inclusion bodies.

FIG. 3B shows the transfer to the nitrocellulose membrane (Western blot) when incubated with serum from diseased pigs infected with *L. intracellularis*.

SUMMARY OF THE INVENTION

Figure 1:
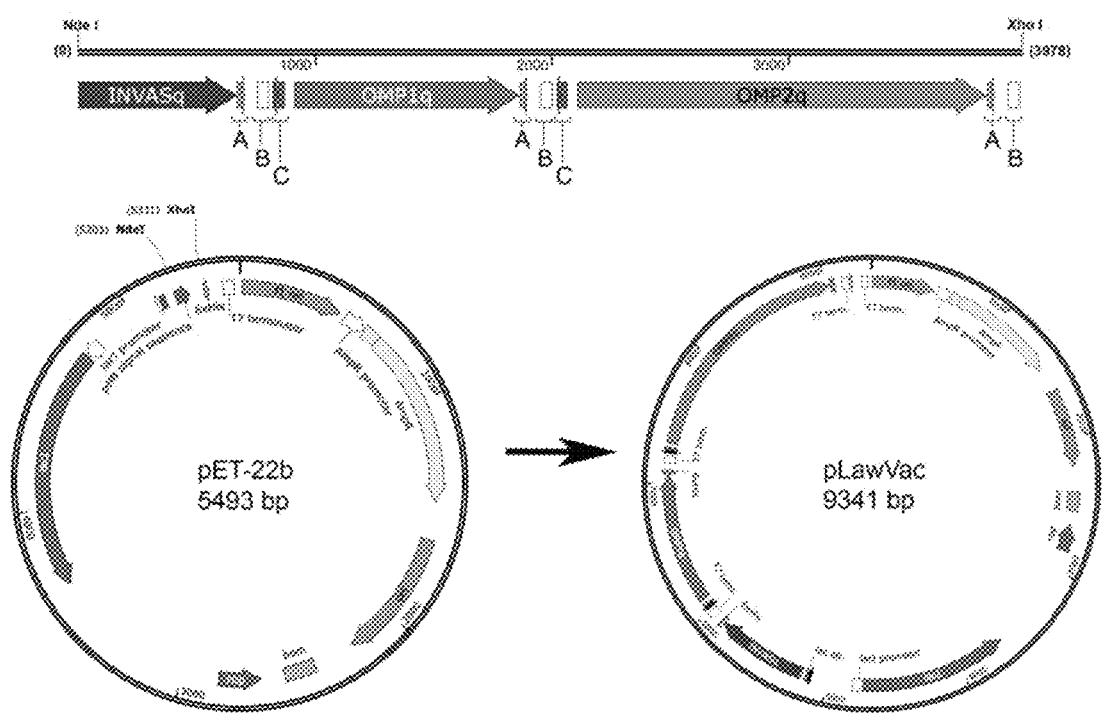
FIG. 1: Representation of the expression cassette of the synthetic antigens Invasq, OMP1q, and OMP2q, and their insertion into the vector pET-22b®. Wherein FIG. 1A corresponds to the spacer/6×His.

The present invention provides a nucleotide sequence encoding an antigen of a bacterium of the genus *Lawsonia*, which comprises: a) a nucleotide sequence encoding a protein selected from the group consisting of an invasin and an outer membrane protein, or a fragment thereof; and b) a nucleotide sequence encoding an epitope for the recognition of T or B lymphocytes, which is selected from the group consisting of the peptide sequences SEQ ID NO: 8, SEQ ID NO: 9, and SEQ ID NO: 10 or a combination thereof. Said outer membrane protein of *Lawsonia* is OMP1 or OMP2.

In a preferred embodiment of the present invention, the synthetic invasin sequence comprises the sequence SEQ ID NO: 1 or any variant derived therefrom; the synthetic outer membrane protein sequence OMP1 comprises the sequence SEQ ID NO: 2 or any variant derived therefrom; and the synthetic outer membrane protein sequence OMP2 comprises the sequence SEQ ID NO: 3 or any variant derived therefrom.

A second object of the present invention is an antigen of a bacterium of the genus *Lawsonia*, which is a synthetic protein comprising: a) a protein selected from the group consisting of an invasin and an outer membrane protein, or a fragment thereof; and b) an epitope for the recognition of T or B lymphocytes, whose peptide sequence is selected from the group consisting of SEQ ID NO: 8, SEQ ID NO: 9, and SEQ ID NO: 10, or a combination thereof. In a preferred embodiment, the synthetic invasin sequence comprises the sequence SEQ ID NO: 4 or any variant derived therefrom; the synthetic outer membrane protein sequence OMP1 comprises the sequence SEQ ID NO: 5 or any variant derived therefrom; and the synthetic outer membrane protein sequence OMP2 comprises the sequence SEQ ID NO: 6 or any variant derived therefrom.

A third object relates to an expression cassette encoding an antigen of a bacterium of the genus *Lawsonia*, comprising: a) a nucleotide sequence promoting transcription; b) a nucleotide sequence encoding an antigen of a bacterium of the genus *Lawsonia* corresponding to a synthetic sequence comprising: i) a nucleotide sequence encoding a protein selected from the group consisting of an invasin and an outer membrane protein, or a fragment thereof; and ii) a nucleotide sequence encoding an epitope for the recognition of T or B lymphocytes, which is selected from the group consisting of the peptide sequences SEQ ID NO: 8, SEQ ID NO: 9, and SEQ ID NO: 10 or a combination thereof; wherein said nucleotide sequence encoding the antigen of a bacterium of the genus *Lawsonia* is operatively linked to the nucleotide sequence of a); and c) a transcription terminator operatively linked to the nucleotide sequence of b). In a preferred embodiment, the expression cassette comprises, in tandem repeats, the expression cassettes encoding the synthetic invasin proteins and the synthetic outer membrane proteins OMP1 and OMP2.

A fourth object of the invention is a cell transformed with a nucleotide sequence encoding an antigen of a bacterium of the genus *Lawsonia* comprising an expression cassette that includes a synthetic nucleotide sequence comprising: i) a nucleotide sequence encoding a protein selected from the group consisting of an invasin and an outer membrane protein, or a fragment thereof; and ii) a nucleotide sequence encoding an epitope for recognition of T or B lymphocytes selected from the group consisting of the peptide sequences SEQ ID NO: 8, SEQ ID NO: 9, and SEQ ID NO: 10 or a combination thereof. In a preferred embodiment, said transformed cell is a prokaryotic cell, even more preferred is a bacterium of the *Escherichia coli* species.

A fifth object of the invention is a vaccine against a bacterium of the genus *Lawsonia*, which comprises at least one antigen selected from the group consisting of: a synthetic invasin protein comprising SEQ ID NO: 4 or any variant derived therefrom; a synthetic outer membrane protein OMP1 comprising the sequence SEQ ID NO: 5 or any variant derived therefrom; a synthetic outer membrane protein OMP2 comprising the sequence SEQ ID NO: 6 or any variant derived therefrom; and a combination of the above. Preferably, the vaccine comprises the combination of the three synthetic proteins.

The present invention additionally provides a method for the production of antigens of a bacterium of the genus *Lawsonia*, which comprises the following steps: a) providing an expression cassette operatively inserted into an expression vector, said expression cassette includes a synthetic nucleotide sequence comprising: i) a nucleotide sequence encoding a protein selected from the group consisting of an invasin and an outer membrane protein, or a fragment thereof; and ii) a nucleotide sequence encoding an epitope for recognition of T or B lymphocytes selected from the group consisting of the peptide sequences SEQ ID NO: 8, SEQ ID NO: 9, and SEQ ID NO: 10 or a combination thereof, or a fragment thereof or a combination thereof; b) transforming a cell with the vector of a); and c) obtaining a synthetic antigen from the culture of the transformed cell of b). Preferably, in said method, the expression cassette comprises, in tandem repeats, the expression cassettes encoding the synthetic invasin proteins and the synthetic outer membrane proteins OMP1 OMP2.

DETAILED DESCRIPTION OF THE INVENTION

The present invention provides a recombinant vaccine against proliferative enteropathy in animals, caused by the *Lawsonia intracellularis* bacterium. Said vaccine is based on recombinant antigens whose sequences have been artificially modified to expose antigenic domains on their surfaces for their recognition by T or B lymphocytes. The invention provides a vaccine formulation comprising these antigens with an adjuvant and/or a suitable vehicle.

The vaccine of the present invention is administered in animals susceptible to infection by bacteria of the genus *Lawsonia*, preferably belonging to the species *Lawsonia intracellularis*. In a preferred embodiment, the vaccine is for veterinary use. Preferably, mammals such as nonhuman primates, dogs, rabbits, horses, sheep, rats and mice, hamsters, foxes, deer, and ferrets are found within the diversity of such susceptible animals. In an even more preferred embodiment, the animals are pigs and the like.

The present invention generates potential direct benefits to the health, management, and raising of pigs worldwide. The vaccine can be administered massively in pig farms, in one or two doses, regardless of the age of the animal or its level of previous infection with the *Lawsonia intracellularis* bacterium, that is, it can be administered in healthy or sick animals.

All technical and scientific terms used to describe the present invention have the same meaning understood for a person with basic knowledge in the technical field in question. However, in order to more clearly define the invention, the following terms will be understood as defined below.

"Synthetic", "chimeric" (abbreviated as q), or "artificially modified" sequence will be understood as the nucleotide or amino acid sequence that has a change in its original native sequence, so that it does not exist as such in nature. Within the framework of the present invention, said artificial modification refers to an insertion of an epitope for the recognition of T or B lymphocytes.

"Epitope" or "antigenic determining sequence" will be understood as the part of a protein molecule that is recognized by the T or B lymphocyte receptors.

"Expression cassette" will be understood as a DNA fragment that contains at least one sequence of a gene encoding a protein of interest, between one or more cutting or recognition sites by enzyme restriction.

The term "operably linked" refers to a combination of at the least two elements, in this case, gene or nucleotide sequences, which are in a location with respect to the other so that they operate in the foreseen manner.

"Vector" will be understood as the DNA molecule capable of hosting a fragment of exogenous or endogenous DNA, or a mixture thereof.

The term "tandem repeat" refers to a DNA fragment that is repeated side by side throughout the sequence.

The present invention relates to a vaccine or vaccine composition and a method for the production of the antigens of said vaccine against infection and the pathologies associated with *Lawsonia intracellularis*, the causative agent of proliferative enteropathy in animals. The vaccine includes new recombinant synthetic antigens that correspond to variants of the membrane proteins OMP1 and OMP2 and invasin, which have been artificially modified with at least one coding sequence of an epitope for the recognition of T or B lymphocytes. The vaccine can include one of these synthetic antigens, or a combination thereof. In a preferred embodiment of the present invention, the vaccine comprises a mixture of the three modified antigens OMP1, OMP2, and invasin.

The present invention provides synthetic DNA nucleotide sequences encoding protein variants of a bacterium of the *Lawsonia* genus, preferably *Lawsonia intracellularis*, which have been artificially modified with at least one sequence encoding an epitope for the recognition of T or B lymphocytes selected from the group consisting of the peptide sequences SEQ ID NO: 8, SEQ ID NO: 9, and SEQ ID NO: 10 or a combination thereof.

The invention also provides proteins or synthetic protein antigens encoded by the previously mentioned synthetic nucleotide DNA sequences, wherein said synthetic antigens may include one or more of the indicated epitopes, inserted at any position within the native protein sequence. In a preferred embodiment, said epitopes are inserted into regions of the proteins that form loops. In another preferred embodiment, said epitopes replace or substitute epitopes that have low allele coverage of the Major Histocompatibility Complex (MHC).

In an embodiment of the invention, the following Table 1 identifies synthetic DNA nucleotide sequences and their corresponding encoded amino acid sequences. Nucleotide sequences are provided in the 5' to 3' direction of the coding DNA strand, which is complementary to the transcribed non-coding template strand. The DNA coding strand is identical to the messenger RNA molecule that is synthesized in the transcription process, the latter having uracil (U) instead of the nitrogenous bases of thymine (T).

TABLE 1

Antigens nucleotide and amino acid sequences.

| Name | Nucleotide sequence | Amino acid sequence |
|---|---|---|
| Synthetic Invasin (Invasq) | SEQ ID NO: 1 | SEQ ID NO: 4 |
| Synthetic OMP1 (OMP1q) | SEQ ID NO: 2 | SEQ ID NO: 5 |
| Synthetic OMP2 (OMP2q) | SEQ ID NO: 3 | SEQ ID NO: 6 |

The nucleotide and amino acid sequences of the synthetic or chimeric protein antigens Invasin, OMP1, and OMP2, called "Invasq", "OMP1q", and "OMP2q", respectively; wherein the modifications corresponding to the sequences of the artificially inserted epitopes are shown in the Sequence Listing, indicating the positions where they were included. Said epitopes were inserted in replacement of an epitope with low allele coverage of the Major Histocompatibility Complex (MHC).

The invention additionally provides an expression cassette encoding a *Lawsonia intracellularis* antigen comprising a nucleotide sequence of transcription promoter DNA, a nucleotide sequence encoding a synthetic antigen of said bacterium, and a nucleotide sequence of transcription terminating DNA. All the elements of the expression cassette are operatively linked to each other, in a way that transcription of the coding sequence in a biological system is possible therefrom. The promoter sequence is found upstream of the coding sequence, while downstream of the latter the transcription terminator sequence is found. The expression cassette may contain at least one sequence encoding the synthetic proteins Invasq, OMP1q, or OMP2q according to the present invention. The promoter sequence can be constitutive or inducible. By way of example, some promoters known in the state of the art useful for these purposes are the promoter of gene lacI, lac/lac UV5, lac/lac UV5, tac/trc, T7/T7/lac, or variants thereof, or others known to any person skilled in the art.

In a preferred embodiment, the expression cassette comprises, in tandem repeats, the expression cassettes encoding the synthetic invasin proteins and the synthetic outer membrane proteins OMP1 and OMP2, that is, side by side. There may optionally be other elements among them, such as reporter genes, selection marker coding genes, restriction enzyme cutting sites, multiple cloning sites, signal sequences for the destination of the produced proteins, markers to facilitate the purification of the produced proteins, among others widely known in the state of the art. Said expression cassettes encoding the synthetic proteins Invasq, OMP1q, and OMP2q can be positioned in any order.

The expression cassette of the present invention can be operatively inserted into an expression vector in order to transform a suitable host and produce the synthetic antigen of the present invention; or it can be inserted into a cloning vector in order to obtain copies thereof in a suitable host. Preferably, said suitable host is a prokaryotic cell. In a preferred embodiment, said cell is the bacterium *Escherichia coli*. Molecular biology techniques for carrying out such manipulations are widely known in the state of the art and by any person skilled in the art. For reference, the following document Rosano, G. L., and Ceccarelli, E. A. (2014), *Recombinant protein expression in Escherichia coli: advances and challenges, Front Microbiol.* 2014; 5: 172 indicates a standard protocol for obtaining recombinant proteins in *Escherichia coli*. The expression of the antigens of interest can be directed to any compartment of the cell. Notwithstanding the foregoing, any expert in the technical field would understand that it is possible to use a wide range of prokaryotic, eukaryotic host cells, or even incorporate said expression cassette into a viral vector for the subsequent infection of a suitable host. Alternatively, the expression cassette of the present invention can be used as part of a DNA vaccine for the production of recombinant antigens in the animals of interest susceptible to infection by *Lawsonia intracellularis*. Optionally, the synthetic protein antigens of the present invention can be expressed in innocuous proteins capable of assembly to form virus-like particles (VLP).

Another object of the present invention is a vaccine or vaccine composition against a bacterium of the genus *Lawsonia*, preferably *Lawsonia intracellularis*. Said vaccine comprises at least one synthetic antigen selected from the group consisting of: a synthetic invasin protein, OMP1 or OMP2, which have been artificially modified according to the present invention to include at least one epitope for the recognition of T or B lymphocytes selected from the group consisting of the peptide sequences SEQ ID NO: 8, SEQ ID NO: 9, and SEQ ID NO: 10 or a combination thereof. In a preferred embodiment, the synthetic invasin sequence comprises SEQ ID NO: 4 or any variant derived therefrom; the synthetic outer membrane protein OMP1 comprises sequence SEQ ID NO: 5 or any variant derived therefrom; the synthetic outer membrane protein OMP2 comprises sequence SEQ ID NO: 6 or any variant derived therefrom. In an even more preferred embodiment, the vaccine comprises a mixture of the three aforementioned synthetic protein antigens. The mixture may comprise said three antigens in any proportion, preferably equivalent proportions 1:1:1. Optionally, the vaccine may include an interferon for potentiating the immune response.

The vaccine of the present invention includes a synthetic antigen in amounts ranging between 100 and 200 µg. The vaccine can be used in conjunction with any oily or other adjuvant that is potentially immunogenic in pigs, which are known in the state of the art. By way of reference, the publication Heegaard, P. M. et al. (2011), *Adjuvants and delivery systems in veterinary vaccinology: current state and future developments. Archives of virology*, 156(2), 183-202 discloses adjuvants for these purposes. By way of example, adjuvants Montanide ISA 15A VG, Adyuvac 70, Montanide 888, Freund's adjuvant can be used. In another preferred embodiment, the synthetic antigens can be co-administered with the immunopotentiating cytokine porcine interferon alfa (pIFN-α) in a proportion ranging between 100-300 µg to further enhance the immune response of the animals, finally obtaining a mixture of synthetic antigens, interferon alfa, and adjuvant in a ratio of 80:20 v/v, where 80% of volume corresponds to the synthetic antigen components and interferon alfa. Optionally, the vaccine may include a pharmaceutical vehicle that allows obtaining a pharmaceutical form suitable for administration in pigs, such as capsules, microcapsules, nanoparticles, liposomes, among others.

The route of administration may be intramuscular, subcutaneous, or intradermal injection, transdermal, and others such as intraperitoneal, intravenous, oral, or even by inhalation. It can be administered in at least one dose, and optionally, booster vaccinations can be provided to the animal. The vaccine can be administered at any age of the animal. In a preferred embodiment, the age range of the pigs to be vaccinated can vary between 15 and 30 days of life, preferably prior to weaning.

Another object of the present invention is a method for the production of *Lawsonia intracellularis* antigens, comprising the steps of: providing an expression cassette encoding the synthetic antigens of the invention, operatively inserted into an expression vector; transforming a host cell with said vector and obtaining a synthetic antigen from the culture of said transformed cell. In a preferred embodiment, said host cell is *Escherichia coli*. As mentioned earlier, the transformation and cultivation techniques of *E. coli* are widely known in the state of the art. For reference, the publication Sivashanmugam, A. et al. (2009), *Practical protocols for production of very high yields of recombinant proteins using Escherichia coli, Protein Science,* 18(5), 936-948, provides protocols and culture media for obtaining recombinant proteins in this host.

In a preferred embodiment, synthetic antigens derived from *Lawsonia* can be purified as inclusion bodies from a previously transformed *E. coli* culture. Inclusion bodies can be used in vaccines as they present immunologically dominant sequences. The use of the synthetic protein antigens of the present invention as inclusion bodies is of great advantage since it is not necessary to re-naturalize the proteins after their extraction. The procedures for obtaining inclusion bodies from *E. coli* are known in the state of the art, where, for reference, the publication Promdonkoy, B. et al. (2004), *Production of a biologically active growth hormone from giant catfish (Pangasianodon gigas) in Escherichia coli, Biotechnology Letters,* 26(8), 649-653 discloses a useful protocol for this purpose.

Having described the preferred embodiments of the invention, referring to the figures included in the description, it will be understood that the invention is not limited to said preferred embodiments, and that any person skilled in the art could make modifications, while maintaining the essence of the invention.

Examples of embodiment of the invention are presented below, which have been included for the purpose of illustrating the invention, its preferred embodiments, and comparative examples, but in no case should they be considered to restrict the scope of the patent application, which is only delimited by the content of the claims attached herein.

APPLICATION EXAMPLES

Example 1: Prediction of Protective Antigens of *Lawsonia intracellularis* in Silico The complete genome sequence of the strain *Lawsonia intracellularis* PHE/MN1 was analyzed using the NCBI Finder Open Reading Frame tool to find open reading frames. From the identification of 1,340 sequences that potentially encode proteins, those corresponding to membrane and secretion proteins were identified by bioinformatics tools (DTU Bioinformatics, DTU Health Tech). Through this analysis, 33 sequences corresponding to secretion proteins and 306 membrane proteins were identified. From the latter, 123 corresponded to type I.

From the previously identified proteins, epitope prediction was performed for the recognition of B and T lymphocytes. B epitopes were identified using the ABCpred and BCEpred tools (Saha S. and Raghava G. P. S. CSIR-Institute of Microbial Technology, IMTechRaghava), applying a cut-off value greater than 0.9. 28 proteins with at least five B epitopes with these characteristics were selected. From these proteins, T epitopes were identified with potential recognition in an MHC-class I context, to enhance the Th1 response, using the NetMHC tool of the CBS server, having as criteria a coverage greater than 50% for all MHC alleles evaluated.

The selection of proteins to be expressed in *E. coli* was carried out taking into account the proteins having molecular weight less than 70 kDa, according to the life cycle and the pathogenesis of the *Lawsonia intracellularis* bacterium. In addition, three T epitopes with 100% coverage were inserted for each MHC allele. These epitopes were included in regions that formed bonds with these proteins and were always replacing a T epitope with low coverage. In this way, the synthetic nucleotide and amino acid sequences of the present invention, corresponding to the Invasq protein antigens and the outer membrane proteins OMP1q and OMP2q, were obtained; those that include the epitope sequences SEQ ID NO: 8, SEQ ID NO: 9, and SEQ ID NO: 10 for the recognition of T or B lymphocytes.

Example 2: Design of an Expression Cassette of the Synthetic Antigens Invasq, OMP1q, OMP2q Once the synthetic or chimeric protein antigens Invasq, OMP1, and OMP2 were designed from the coding nucleotide sequences (or genes), an expression cassette was designed for its subsequent cloning into a vector. The sequence SEQ ID NO: 7 shows said expression cassette, wherein the regulatory elements of transcription are indicated. As a preferred embodiment, said cassette included, in tandem repeats, synthetic nucleotide sequences encoding the mentioned synthetic antigens, each with its promoter and terminator sequence operatively linked. The expression cassette was cloned into the expression vector pET22b (+) (Novagen®) between restriction sites NdeI and XhoI. FIG. 1 shows a representation of the expression cassette inserted in the mentioned vector, which was named pLawVac. Each protein has a repeat sequence of the amino acid histidine to facilitate purification in a metal ion binding matrix.

Example 3: Production of Synthetic Antigens from *Lawsonia* Intracellularis

Expression of Synthetic Antigens in *E. coli*.

The expression vector obtained above (pLawVac) which includes the expression cassette of the three synthetic antigens Invasq, OMP1, and OMP2, was used to transform a culture of the strain *Escherichia coli* K12 (SHuffle® T7, New England Biolabs). The transformation with the vector (100 µL of culture/100 ng of vector) was carried out by means of a thermal shock at 42° C. for 2 minutes and then the bacteria were seeded on agar-LB-ampicillin plates (0.1 µg/mL) at 37° C. for 16 hours. Induction of protein expression was performed with 0.5 mM isopropyl β-D1-thiogalactopyranoside (IPTG). The culture was maintained for 12 hours and then centrifuged at 4,330 g for 15 minutes to obtain the bacteria in a precipitate or pellet. The bacteria were resuspended in a phosphate buffered saline solution (50 mM $NaH_2PO_4$, 300 mM NaCl, 8 M urea) and then a cell rupture was performed using a French EmulsiFlex C-5 press, Avestin, Inc (900 psi) in the presence of 8 M urea. Finally, the supernatant was recovered, centrifuging at 15,000 g for 20 minutes at 4° C.

Figure 2:
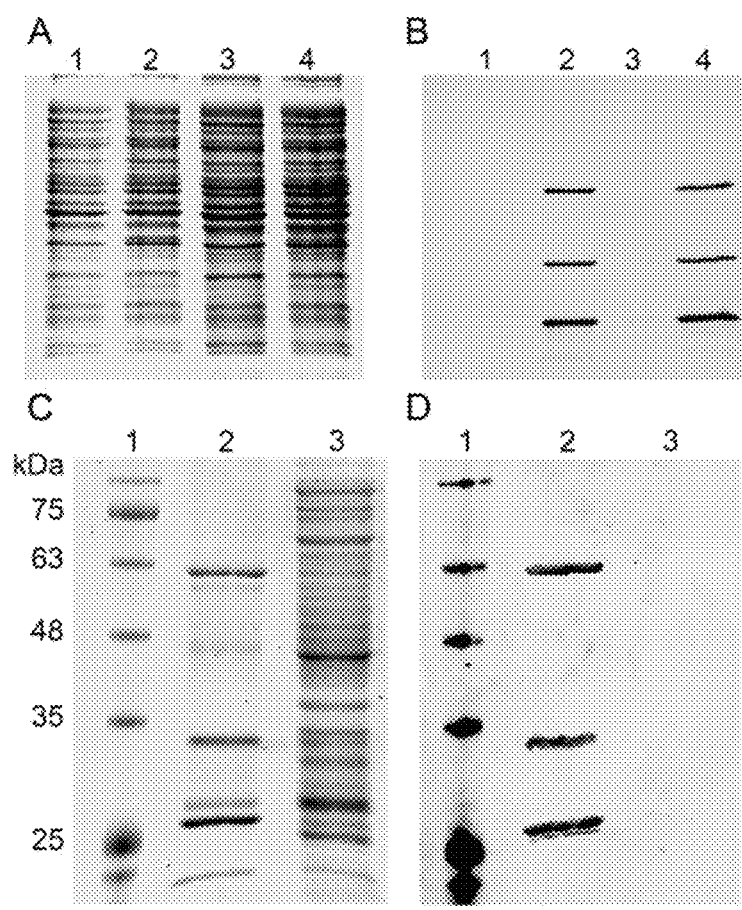
FIG. 2: Gel electrophoresis of proteins (SDS-PAGE) stained with Coomassie blue (FIGS. 2A and 2C) corresponding to the synthetic antigens Invasq, OMP1q, and OMP2q expressed in *E. coli*; and Western blot (FIGS. 2B and 2D).

The supernatant was analyzed by a 12% electrophoresis gel under denaturing conditions (SDS-PAGE) and subsequent transfer to nitrocellulose membrane (Western blot) to evaluate the intracellular expression of synthetic antigens. Samples were taken at 6 and 12 hours after induction. As shown in FIG. 2A (Coomassie blue staining) and B (Western blot), the three proteins Invasq, OMP1q, and OMP2q, corresponding to molecular weights of approx. 25, 35, and 65 kDa respectively (lanes 2 and 4, 6 and 12 hours after induction, respectively) were expressed. Lanes 1 and 3 show the supernatant of cell rupture of non-transformed bacteria as a control. Mouse anti-histidine (Clontech laboratories, USA) was used as primary antibody, and labeled anti-mouse (Alexa Fluor 680, Jackson, USA) was used as secondary antibody. The bands were visualized at a wavelength of 680 nm, using an image capture system (Odyssey System, LI-COR, Bioscience).

In parallel, synthetic antigens were obtained as inclusion bodies from the previously transformed *E. coli* culture. For this, it was used the protocol of Promdonkoy, B. et al. (2004), *Production of a biologically active growth hormone from giant catfish (Pangasianodon gigas) in Escherichia coli, Biotechnology Letters*, 26(8), 649-653. FIG. 2C shows an SDS-PAGE gel of said antigens (lane 1) stained with Coomassie blue, and in D the Western blot transfer is shown following the same experimental procedure. Lanes marked with a 1 in FIGS. 2C and 2D show the molecular weight pattern.

Recognition of Specific Antibodies in Serum from Infested Pigs.

Figure 3:
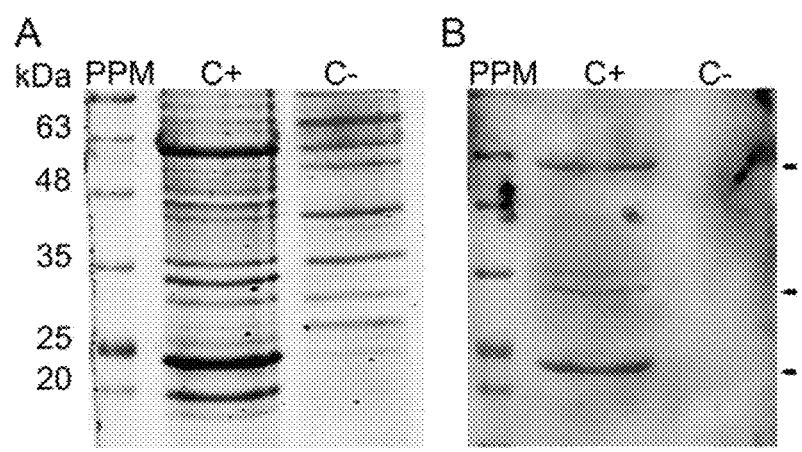
FIG. 3: Polyacrylamide gel electrophoresis (SDS-PAGE) of synthetic antigens (FIG. 3A), (positive control C+) Invasq, OMP1q, and OMP2q expressed in the rupture supernatant of transformed *E. coli*, and of the rupture supernatant of the unprocessed bacterium (negative control C−).

The rupture supernatant of the strain *E. coli* SHuffle® T7, which contains the protein antigens of *Lawsonia* (C+) and the rupture supernatant of the unprocessed bacteria (C−) were analyzed in polyacrylamide gel electrophoresis (SDS-PAGE, FIG. 3A) and transferred to nitrocellulose membrane (Western blot, FIG. 3B). As primary antibody, serum from diseased pigs infected with *L. intracellularis* was used, and as secondary antibody labeled anti-pig (Alexa fluor 680, Jackson, USA) was used. The results showed bands at the expected electrophoretic height according to the molecular weight of the three *Lawsonia* proteins (Invasq, OMP1q, OMP2q: 25, 35, and 65 kDa, respectively). No signal was observed in the untransformed *E. coli* sample, used as a negative control. This result is of great relevance as it confirms the predictions on which the bioinformatic design was made for the inclusion of potentially immunogenic sequences in the expression vectors.

Example 4: Immunological Assays with the Synthetic Protein Antigens Invasq, OMP1q, and OMP2q Evaluation of the Immune Response in Mice Immunized with the *Lawsonia* Inclusion Bodies.

Figure 4:
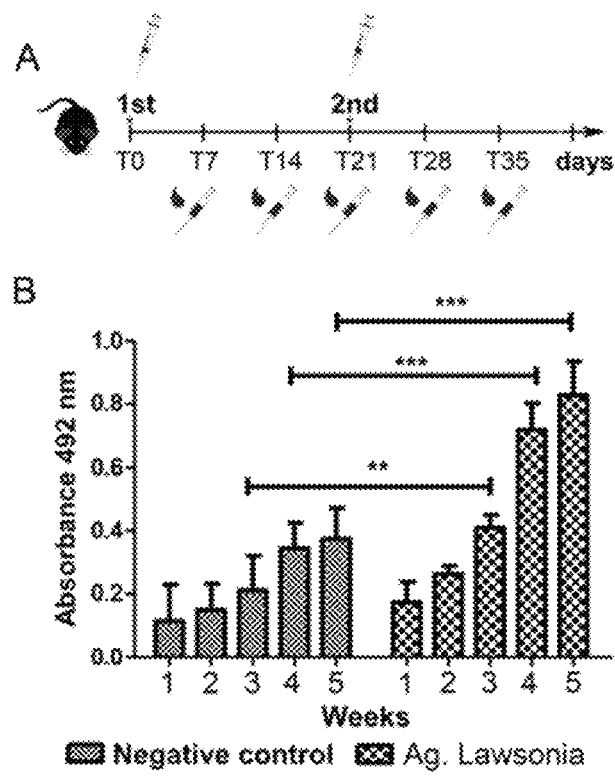
FIG. 4: Immunization scheme of mice with the synthetic protein antigens Invasq, OMP1q, and OMP2q as inclusion bodies (FIG. 4A). Absorbance reading in an ELISA assay using samples of mice immunized via intramuscular route (FIG. 4B).

Female C57BL/6 mice were immunized with 50 µg of the synthetic protein antigens as inclusion bodies dissolved in PBS saline. As a negative control, inclusion bodies of untransformed *E. coli* bacteria were used. Immunization was performed intramuscularly. As adjuvants, Montanide® ISA 15A VG (Seppic) was used in an antigen:adjuvant ratio (80:20) and 100 µL were administered. The first immunization was performed on day 1 of the assay and then a second immunization on day 21. Blood samples were taken every 7 days from the start of the test until day 35 of the assay (FIG. 4A). Experimental groups of 5 mice each were made to assess the humoral response of the antigen with respect to the negative control group.

The evaluation of the IgG response (in serum) in mice after the administration of two 50 µg doses of the inclusion bodies of the *Lawsonia* synthetic antigens Invasq, OMP1q, and OMP2q via intramuscular route was performed by indirect ELISA. For this, plates were coated with 100 µL of the inclusion bodies, solubilized with 8 M urea (10 µg/mL) overnight at 4° C. 1/100 diluted mouse serum was used as the primary antibody, and goat anti-mouse IgG conjugated to peroxidase (1/10,000) was used as a secondary antibody. The reading was performed at a wavelength of 492 nm. The proteins of the non-transformed bacteria were used as a control in the experiment. The results showed significant differences in mice immunized via intramuscular route with synthetic protein antigens compared to mice immunized with the inclusion bodies of unprocessed bacteria, from the third week after conducting the second immunization (FIG. 4B).

Evaluation of the Functionality of Synthetic Protein Antigens.

Figure 5:
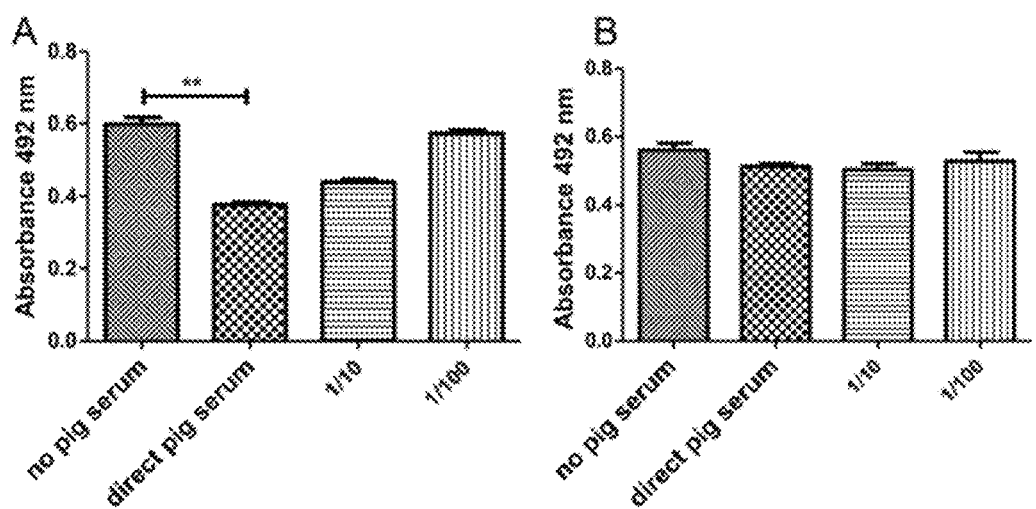
FIG. 5: Design of a competitive ELISA assay, between serum from diseased pigs (pig+) and mice immunized (mouse+) with the synthetic protein antigens Invasq, OMP1q, and OMP2q (FIG. 5A); and healthy pigs (pig−) and immunized mice (mouse+) (FIG. 5B).

The functionality of the recombinant antigen was evaluated by a competitive ELISA assay (FIG. 5). The experiment was performed by coating an ELISA plate with synthetic protein antigens (Invasq, OMP1q, OMP2q) obtained as solubilized inclusion bodies and incubating with different serum concentrations from farm pigs diseased due to *Lawsonia* infection. It was subsequently incubated with the serum from mice immunized with synthetic protein antigens as indicated above. As a secondary antibody, a goat anti-mouse IgG polyclonal antibody conjugated to peroxidase (Abcam, UK) was used. In this way, a decrease in measured absorbance reflects the competition between the primary antibodies that recognize the antigens.

FIG. 5 shows the results of the absorbance values, from which the value obtained by using serum from mice immunized with the inclusion bodies of the non-transformed bacteria as controls was subtracted. The statistical analysis used was the Kruskal-Wallis test followed by Dunn post-hoc test (**$p<0.01$). The results indicated in FIGS. 5A and 5B show that antibodies generated in mice immunized with synthetic protein antigens (mouse+) compete with the antibodies present in the serum from diseased pigs (pig+, FIG. 5A). The significant decrease in absorbance (492 nm) obtained when previously incubated with mouse sera (without dilution), indicates that the antibodies present in the serum from infested pigs and in the serum from mice immunized with synthetic protein antigens, share epitopes present in recombinant synthetic protein antigens. This behavior varies when serial dilutions of the sera from infested pigs are used, resulting in that the higher the dilution of pig serum, the competition decreases, and therefore the absorbance difference also decreases. When performing the competition test with serum from healthy pigs (pig−) as a control, no decrease in absorbance was observed, as expected (FIG. 5B). This result is very important as it suggests that the synthetic protein antigens of the present invention as candidates for formulating a vaccine are specific and effective.

Evaluation of the Immune Response in Pigs Immunized with the *Lawsonia* Inclusion Bodies.

Eight healthy pigs were immunized three weeks after weaning, with 200 µg of antigen per animal via intramuscular route with a formulation containing inclusion bodies with the synthetic protein antigens Invasq, OMP1q, and OMP2q at a concentration of 200 µg/mL obtained in *E. coli* (T0), and at 21 days a booster immunization (T21) is performed, according to FIG. 6A. The antigens were mixed with the adjuvant Montanide ISA 15A VG in an 80:20 ratio. As a negative control group, eight pigs were used, to which negative proteins of bacteria were injected. Additionally, an experimental group (n=8) was tested, where pigs were administered an emulsion consisting of a mixture of synthetic antigens, porcine interferon alfa, and adjuvant, maintaining the aqueous solution:montanide ratio of (80:20).

The immune response (IgG antibodies) was quantified from week 1 (T7) and until week 6 (T42) by serum samples taken from T7 to T42 every 7 days and by indirect ELISA analysis. For this, plates were sensitized with the solubilized *Lawsonia* synthetic protein antigens (Invasq, OMP1q, and OMP2q). The data in FIG. 6B show the absorbance obtained in the indirect ELISA assay for pig IgG, by analyzing the sera from animals immunized with the *Lawsonia* synthetic antigens, the mixture of synthetic antigens plus porcine interferon alfa, and the control group. The result showed significant differences from the fourth week of the assay after the booster dose, where it was observed that the administration of the synthetic antigens Invasq, OMP1q, and OMP2q as vaccine produces an IgG response in pigs significantly greater than the negative control group. Additionally, it was observed that by including porcine interferon alfa in the immunization mixture, an IgG immune response significantly greater than the previous groups was obtained. The above indicates that vaccinated pigs are capable of producing antibodies against recombinant synthetic protein antigens (Invasq, OMP1q, and OMP2q) of *Lawsonia intracellularis*, in accordance with the present invention. Moreover, the addition of interferon alfa in the preparation significantly increased the IgG response with respect to the group that was only administered the mixture of synthetic antigens.

Figure 7:
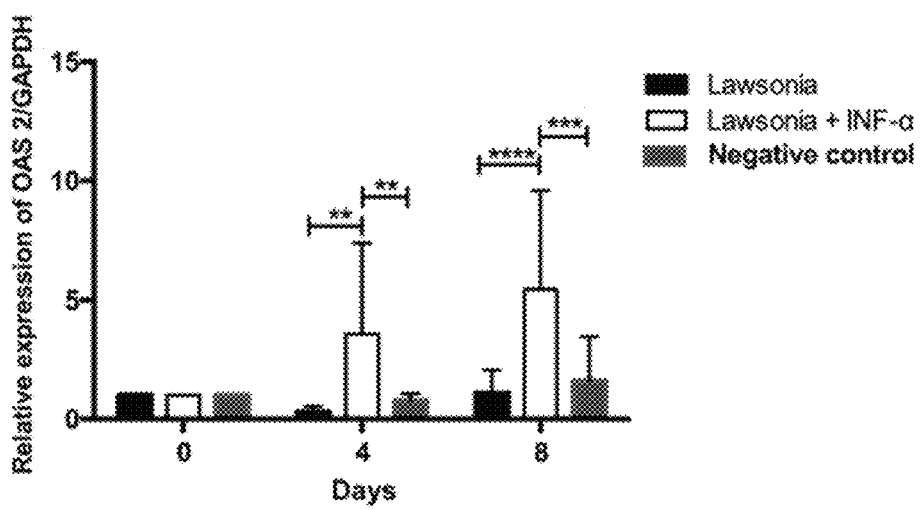
FIG. 7: Quantification of the relative expression of the OAS2/GAPDH gene. The statistical analysis used was the Two-Way ANOVA test with post-hoc Tukey's multiple comparison test (**$p \leq 0.0001$, *$p \leq 0.001$, **$p \leq 0.01$).

The activity of interferon alfa in the immunization mixture was determined by measuring the differential expression of the gene Oligoadenylate Synthetase (OAS2) by real time PCR in the 8 pigs of each experimental group at 0, 4, and 8 days after the first immunization. For this, the expression of the GAPDH gene was used as the reference gene (FIG. 7). The interaction of interferons alfa/beta with their receptor results in the transcription of genes (e.g. OAS) responsible for inducing the response of the immune system through the degradation of the genetic material of the pathogen in the infested cells. From the lymphocytes, extracted from peripheral blood, the RNA was purified by a standardized protocol (TRIzol, Invitrogen), and the first complementary DNA chain using the RevertAid™ Reverse Transcriptase reagent (M-MuLV RT, Thermo) was obtained by reverse transcription. The relative expression of the gene OAS2 was analyzed with respect to the reference gene GAPDH, said gene being indicative of antiviral activity.

Figure 6:
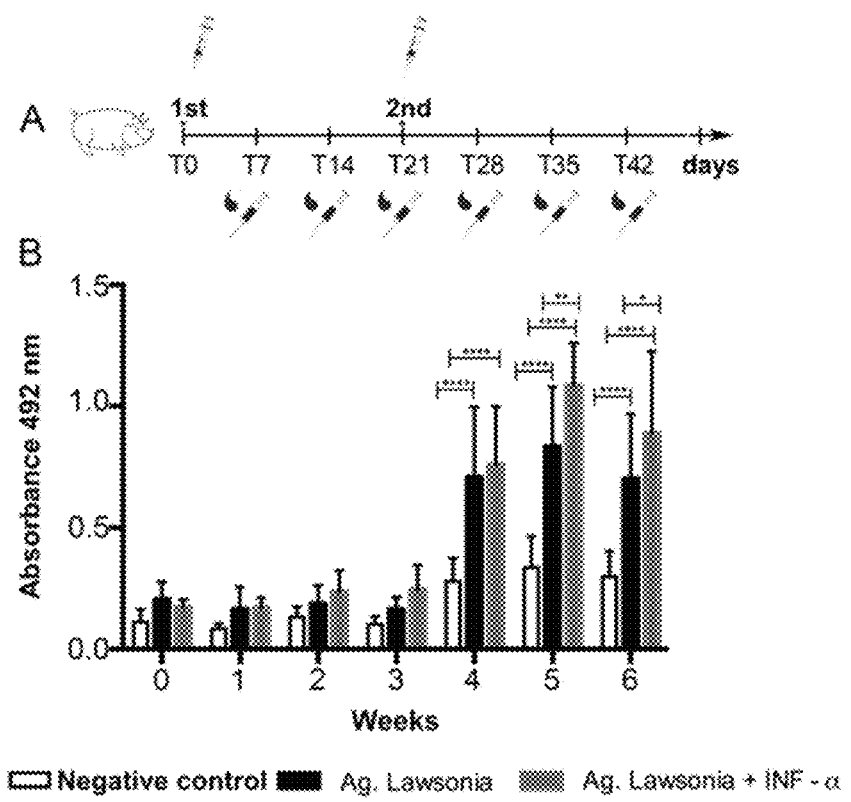
FIG. 6: Scheme of immunization of pigs with the synthetic protein antigens Invasq, OMP1q, and OMP2q (FIG. 6A). Indirect ELISA assay to evaluate the immune response of pigs under different conditions (FIG. 6B).

The results showed significant differences in the expression of the gene OAS2 on day 8 after the first inoculation in the group immunized with the formulation containing the synthetic protein antigens Invasq, OMP1q, and OMP2q plus interferon alfa, with respect to the group immunized with the mixture of antigens that do not contain the cytokine and the control group. The result indicates the activation of the immune system, specifically the humoral immune response expressed by increased IgG, as shown in FIG. 6, by including porcine interferon alfa in the immunization mixture.

Evaluation of the Cellular Immune Response in Pigs Immunized with the *Lawsonia* Inclusion Bodies.

Figure 8:
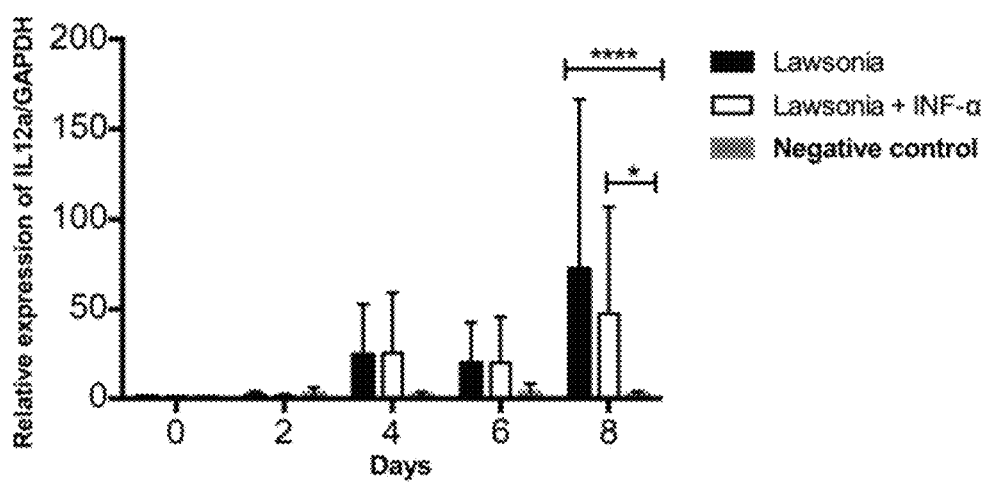
FIG. 8: Quantification of the relative expression of the IL-12a/GAPDH gene. For statistical analysis of the results, the Two-Way ANOVA test with post-hoc Tukey's multiple comparison test was used (***p≤0.001, *p≤0.05).

The cellular response of the three experimental groups of assays with pigs was evaluated by measuring the proinflammatory cytokine IL-12. The differential expression of the gene coding for IL-12 was determined by real-time PCR in the 8 pigs of each experimental group at 0, 2, 4, 6, and 8 days after the first immunization using the expression of the gene GAPDH as the gene of reference (FIG. 8). For this, peripheral blood lymphocytes (PBL) were extracted, and from said lymphocytes the RNA was purified by a standardized protocol (TRIzol, Invitrogen). Once the RNA was purified, reverse transcription was performed to obtain the first complementary DNA strand using the RevertAid™ Reverse Transcriptase reagent (M-MuLV RT, Thermo).

The results showed a significant increase in the relative expression of IL12/GAPDH at 8 days after the first immunization of the groups immunized with the formulation containing the synthetic antigens (****p≤0.0001) and the formulation that also incorporates the interferon alfa (*p≤0.05) with respect to the negative control group. The increase in proinflammatory IL-12 shows the development of a Th1-type cellular response.

Example 5: Protective Assays in Pigs Immunized with the Synthetic Protein Antigens Invasq, OMP1q, and OMP2q Against Exposure to the *Lawsonia Intracellularis* Bacterium The evaluation of protection against infection with *L. intracellularis* was performed in two experimental groups described in Example 4, of 8 pigs each; the group immunized with the synthetic protein antigens Invasq, OMP1q, and OMP2q, co-formulated with the porcine interferon alfa, and the negative control group. After 55 days from the first immunization, all animals in both groups were orally administered a dose of 40 mL of a macerated ileum from an animal naturally infected with *L. intracellularis*. The presence of *L. intracellularis* in the macerated tissue, which was used as inoculum, was checked by Histopathology and Immunohistochemistry. The monitoring of the animals of both groups under study was conducted every other day, through the observation of clinical signs and the behavior of the animals during the challenge test.

After 30 days of inoculation, blood and serum samples were taken, and subsequently all animals were sacrificed to conduct a necropsy. At necropsy, alteration of the gastrointestinal tract was observed in animals of the negative group with respect to the group immunized with protein antigens plus interferon alfa. The histopathological study was carried out using traditional and immunohistochemical techniques, with protection against infection with the *L. intracellularis* bacterium being observed only in the animals of the vaccinated group.

The invention claimed is:

1. A nucleotide sequence encoding an antigen of a bacterium of genus *Lawsonia*, said nucleotide sequence is selected from the group consisting of SEQ ID NO: 1, SEQ ID NO: 2, and SEQ ID NO: 3.

2. An expression cassette encoding an antigen of a bacterium of genus *Lawsonia*, comprising:
   a) a promoter;
   b) a nucleotide sequence selected from the group consisting of SEQ ID NO: 1, SEQ ID NO: 2, and SEQ ID NO: 3; and
   c) a transcription terminator operatively linked to said nucleotide sequence.

3. A method for producing an antigen of a bacterium of genus *Lawsonia*, comprising:
   a) providing an expression cassette operatively inserted into an expression vector, said expression cassette comprising:
      i. a promoter;
      ii. a nucleotide sequence selected from the group consisting of SEQ ID NO: 1, SEQ ID NO: 2, and SEQ ID NO: 3; and
      iii. a transcription terminator operatively linked to said nucleotide sequence;
   b) transforming a cell with said expression vector;
   c) culturing the transformed cell; and
   d) obtaining the antigen from the culture of the transformed cell.

* * * * *

SEQUENCE LISTING

<160> NUMBER OF SEQ ID NOS: 10

<210> SEQ ID NO 1
<211> LENGTH: 666
<212> TYPE: DNA
<213> ORGANISM: Artificial Sequence
<220> FEATURE:
<223> OTHER INFORMATION: Synthetic Invasin
<220> FEATURE:
<221> NAME/KEY: misc_feature
<222> LOCATION: (142)..(168)
<223> OTHER INFORMATION: Nucleotide sequence encoding the epitope
      FSYATDLSY
<220> FEATURE:
<221> NAME/KEY: misc_feature
<222> LOCATION: (550)..(576)
<223> OTHER INFORMATION: Nucleotide sequence encoding the epitope
      FSFPYWFTF
<220> FEATURE:
<221> NAME/KEY: misc_feature
<222> LOCATION: (604)..(630)
<223> OTHER INFORMATION: Nucleotide sequence encoding the epitope
      KQFNLNTLL

<400> SEQUENCE: 1
cagacaggac tttacatcgc gccgaaattt atttggggtt tcgcgccggt cgatatcaaa      60
accacgggta cgattggcat tgtcaatgta cagaccatct ccgatagcgt ctctcataaa     120
aaaacagaat ctcttcccgg tttctcttat gccactgatc ttagttacaa tcacatgttt     180
caaaccccga tccgcaccga gctcgaattt tccttcttta aaaaaatgga tattaaacac     240
aatggacaaa aaactgatat tactctgggc gctttacttg ttaacggcta ttttgatatt     300
aaaaccgatt caccgttcac gccttacatt ggagtaggtt taggaattgc aggagttaaa     360
acaaaaagca acgctattat tgattcactt ggatacgaca tcaaagtaaa actggacgat     420
aaaacaaaaa aaattttgc atggatggca acagtaggca cctcgtatga aatttccgaa      480
acatttgcac tggatctggg ctaccgcttt gcaggcttcg gtaaaggtga gactaaatcc     540
tggaacaaat tctctttccc ttactggttt accttcggcc ccgttaccgc taccgccaac     600
gctaaacaat ttaaccttaa caccttatta atgcatcaga ttatcttatc cgcccgcctt     660
acattt                                                               666

<210> SEQ ID NO 2
<211> LENGTH: 951
<212> TYPE: DNA
<213> ORGANISM: Artificial Sequence

```
<220> FEATURE:
<223> OTHER INFORMATION: Synthetic OMP1
<220> FEATURE:
<221> NAME/KEY: misc_feature
<222> LOCATION: (67)..(93)
<223> OTHER INFORMATION: Nucleotide sequence encoding the epitope
      FSYATDLSY
<220> FEATURE:
<221> NAME/KEY: misc_feature
<222> LOCATION: (231)..(258)
<223> OTHER INFORMATION: Nucleotide sequence encoding the epitope
      FSFPYWFTF

<400> SEQUENCE: 2
```

| | | | | | |
|---|---|---|---|---|---|
| gccgaagtga | cagcctcatg | tacaaaacgc | gtcgaaagtt | acaattatct | tgttgactac | 60 |
| tctggattta | gttatgcgac | cgatctctct | tatcgtgaac | cgaaaattga | attagcaaaa | 120 |
| gaagcgattt | taaaaattaa | tgccgcaatg | cctaagatgt | cataccaagg | tggattatat | 180 |
| accttttgcgc | cttactctgt | aatcatccca | caaggatctt | ggaattcatg | ctttagtttt | 240 |
| ccgtactggt | ttacctttaa | aagcgacctc | gaaatctttg | acgtttgac | cccaatgggc | 300 |
| gatggtatca | aaatgcatga | aacagttatc | aaccaaatgc | cgcctcaagc | cgccgtaatc | 360 |
| ctgttaaccg | atggccataa | caatctcgga | atgaatccag | ttgaagaagt | aaaatcaatc | 420 |
| tatcagacca | atccaaatgt | gtgttttcat | gttgcatcct | ttgccgatga | cgcggaaggt | 480 |
| aaagcgatta | ttgaccaaat | tgttgcgttg | aactcaggta | gtgtactcgt | ggatgggctt | 540 |
| caactcttgc | aaaaccccgc | agtttgtcag | gaattcgtta | acagcgtgtt | ttgccaaggc | 600 |
| cagatccttg | taactgaaga | agtcgtcgtg | ctgcgtggtg | tgaactttgc | ttttgattcg | 660 |
| tttgccctgg | atgatacggc | taaagctatc | agtgaagaaa | cagtccgctt | gattcgtgcg | 720 |
| aaccctgatt | ttaatgttcg | cctgctgggc | tggaccgact | cgacaggccc | ggatgcatat | 780 |
| aatctccgtc | tcagccaaga | acgcgccgat | gccgttaaaa | acttttagt | aaaaatgggt | 840 |
| attccgtcta | accgtctgtt | tgcaaaaggt | atgggtaagt | cttatcaata | caataatgcc | 900 |
| actaaagaag | gccgctatat | gaatcgccgt | accgaattgg | tgttttttga | t | 951 |

```
<210> SEQ ID NO 3
<211> LENGTH: 1728
<212> TYPE: DNA
<213> ORGANISM: Artificial Sequence
<220> FEATURE:
<223> OTHER INFORMATION: Synthetic OMP2
<220> FEATURE:
<221> NAME/KEY: misc_feature
<222> LOCATION: (955)..(981)
<223> OTHER INFORMATION: Nucleotide sequence encoding the epitope
      FSYATDLSY
<220> FEATURE:
<221> NAME/KEY: misc_feature
<222> LOCATION: (1345)..(1371)
<223> OTHER INFORMATION: Nucleotide sequence encoding the epitope
      FSFPYWFTF

<400> SEQUENCE: 3
```

| | | | | | |
|---|---|---|---|---|---|
| tctatcacca | caagtaccat | taatcaacag | catatcgcct | acaccgtaac | tttcacctcc | 60 |
| cctgaaaatc | cgaatttagc | cacggaaatg | gaaacgcata | gtgagcttgt | caaattagcc | 120 |
| aaccaaagcc | tggattcaaa | aatcggtttg | aacctgcgtg | taaaagaaga | catctccacc | 180 |
| gcacaaaaaa | tcctggacag | taacggatat | tatagcggtt | cagttgaggg | taaaatcgat | 240 |
| tggcagacca | accccatcag | tattcagatt | caatttaaac | caaacgtaca | atacaaaatt | 300 |
| aacaccattc | atatccaata | ccttgactcg | gaactggcgt | atttaccgct | cagccttgaa | 360 |

```
gagtttaacc tgtctaaggg caatcccgca ctggccgtga atattttaag ctcggtgagc      420
tctttaatgc aatatattca caataatggt taccccctcg ctaaaatcaa aaagacgcaa      480
tatattatca atcgtatgga ttatacccttt gacatcgatc tggtgatccg tcaaggtccc     540
ttactgcaca tgggcaaagt acaaccgcag cataacctga acatttccac catcttctta     600
aataaaattg caacctggaa agaaggacgc gtatggaata atgcacttct ggactcatat     660
cgcacccgtt tacagcagac cggcctgttt tcttccatta ctctgaaccc gcgcaatcaa     720
aaagaacaga acgggaacac ctctatcgaa ttagtagcaa ccgaagctcc gccacgtacg     780
atttcagggg ggctgcaata ttccagtgat cagggtatcg cgcccgcgg cacctgggaa      840 catcgcaacg ttttttggcaa cggcgaatta ttccgtatca ccgccccaat ttcccgcgac     900
gaccagaaaa ttatggccaa ctttcagaaa ccagcatttg gacgcccaaa tcagttctct     960
tacgccaccg acctctccta caaagagaat accaagtcct acaaacagca actggcaagc    1020
atcgcgttag gtattgaacg tcagtttaac cgccgctggt tcggtagctc ttcgttaagt    1080
gttgatacag gctttatgga tgaccgcgac tcaatcaaaa aaatctttac gctctttggt    1140
attccgctgt caattacacg cgattcgtca aaggacccat taaacccgat ccaggggacc    1200
aaagcaacat taaatgtcac gccctatatt ggtaaataca aaaaaaaaat cctgactctg    1260
cgcagtcgtt tcgattttc tttctatatt gacgtactga aaaccggtaa actgattctg     1320
gcgaataaaa tcgcgattgg ctcgttctct tttccctatt ggtttacatt ccctgcaatt    1380
ttacgttttt acgccggtgg cggcggatct gtacgcggct acgattatca aagcctgggc    1440
ccgaagaata aatacggcga tgccattggc ggcctgtctt tctcaaccat ctccttcgaa    1500
ctgcgtctta aaatcactga gtccatcggg atcgtcccctt ttattgatgg aggtaacatt    1560
tatgaaaaaa aatttcccga ctttaaaaag agcatttatt ggggcgttgg ccttggcctc    1620
cgttattata caagctttgc accaatccgt cttgatatcg ccaccccgtt gcaggaccgc    1680
tcccataaca aacatttcca actgtacatc tccattggac aggcttttt                1728
```

<210> SEQ ID NO 4
<211> LENGTH: 222
<212> TYPE: PRT
<213> ORGANISM: Artificial Sequence
<220> FEATURE:
<223> OTHER INFORMATION: Synthetic Invasin "INVASq"
<220> FEATURE:
<221> NAME/KEY: MISC_FEATURE
<222> LOCATION: (48)..(56)
<223> OTHER INFORMATION: Epitope
<220> FEATURE:
<221> NAME/KEY: MISC_FEATURE
<222> LOCATION: (184)..(192)
<223> OTHER INFORMATION: Epitope
<220> FEATURE:
<221> NAME/KEY: MISC_FEATURE
<222> LOCATION: (202)..(110)
<223> OTHER INFORMATION: Epitope

<400> SEQUENCE: 4

```
Gln Thr Gly Leu Tyr Ile Ala Pro Lys Phe Ile Trp Gly Phe Ala Pro
1               5                   10                  15

Val Asp Ile Lys Thr Thr Gly Thr Ile Gly Ile Val Asn Val Gln Thr
            20                  25                  30

Ile Ser Asp Ser Val Ser His Lys Lys Thr Glu Ser Leu Pro Gly Phe
        35                  40                  45

Ser Tyr Ala Thr Asp Leu Ser Tyr Asn His Met Phe Gln Thr Pro Ile
    50                  55                  60
```

-continued

```
Arg Thr Glu Leu Glu Phe Ser Phe Phe Lys Lys Met Asp Ile Lys His
 65                  70                  75                  80

Asn Gly Gln Lys Thr Asp Ile Thr Leu Gly Ala Leu Leu Val Asn Gly
                 85                  90                  95

Tyr Phe Asp Ile Lys Thr Asp Ser Pro Phe Thr Pro Tyr Ile Gly Val
            100                 105                 110

Gly Leu Gly Ile Ala Gly Val Lys Thr Lys Ser Asn Ala Ile Ile Asp
            115                 120                 125

Ser Leu Gly Tyr Asp Ile Lys Val Lys Leu Asp Asp Lys Thr Lys Lys
            130                 135                 140

Asn Phe Ala Trp Met Ala Thr Val Gly Thr Ser Tyr Glu Ile Ser Glu
145                 150                 155                 160

Thr Phe Ala Leu Asp Leu Gly Tyr Arg Phe Ala Gly Phe Gly Lys Gly
                165                 170                 175

Glu Thr Lys Ser Trp Asn Lys Phe Ser Phe Pro Tyr Trp Phe Thr Phe
            180                 185                 190

Gly Pro Val Thr Ala Thr Ala Asn Ala Lys Gln Phe Asn Leu Asn Thr
            195                 200                 205

Leu Leu Met His Gln Ile Ile Leu Ser Ala Arg Leu Thr Phe
            210                 215                 220
```

<210> SEQ ID NO 5
<211> LENGTH: 317
<212> TYPE: PRT
<213> ORGANISM: Artificial Sequence
<220> FEATURE:
<223> OTHER INFORMATION: Synthetic OMP1 "OMP1q"
<220> FEATURE:
<221> NAME/KEY: MISC_FEATURE
<222> LOCATION: (23)..(31)
<223> OTHER INFORMATION: Epitope
<220> FEATURE:
<221> NAME/KEY: MISC_FEATURE
<222> LOCATION: (78)..(86)
<223> OTHER INFORMATION: Epitope

<400> SEQUENCE: 5

```
Ala Glu Val Thr Ala Ser Cys Thr Lys Arg Val Glu Ser Tyr Asn Tyr
  1               5                  10                  15

Leu Val Asp Tyr Ser Gly Phe Ser Tyr Ala Thr Asp Leu Ser Tyr Arg
                 20                  25                  30

Glu Pro Lys Ile Glu Leu Ala Lys Glu Ala Ile Leu Lys Ile Asn Ala
             35                  40                  45

Ala Met Pro Lys Met Ser Tyr Gln Gly Gly Leu Tyr Thr Phe Ala Pro
 50                  55                  60

Tyr Ser Val Ile Ile Pro Gln Gly Ser Trp Asn Ser Cys Phe Ser Phe
 65                  70                  75                  80

Pro Tyr Trp Phe Thr Phe Lys Ser Asp Leu Glu Ile Phe Gly Arg Leu
                 85                  90                  95

Thr Pro Met Gly Asp Gly Ile Lys Met His Glu Thr Val Ile Asn Gln
            100                 105                 110

Met Pro Pro Gln Ala Ala Val Ile Leu Leu Thr Asp Gly His Asn Asn
            115                 120                 125

Leu Gly Met Asn Pro Val Glu Glu Val Lys Ser Ile Tyr Gln Thr Asn
            130                 135                 140

Pro Asn Val Cys Phe His Val Ala Ser Phe Ala Asp Asp Ala Glu Gly
145                 150                 155                 160
```

```
Lys Ala Ile Ile Asp Gln Ile Val Ala Leu Asn Ser Gly Ser Val Leu
                165                 170                 175

Val Asp Gly Leu Gln Leu Leu Gln Asn Pro Ala Val Cys Gln Glu Phe
            180                 185                 190

Val Asn Ser Val Phe Cys Gln Gly Gln Ile Leu Val Thr Glu Glu Val
            195                 200                 205

Val Val Leu Arg Gly Val Asn Phe Ala Phe Asp Ser Phe Ala Leu Asp
        210                 215                 220

Asp Thr Ala Lys Ala Ile Ser Glu Glu Thr Val Arg Leu Ile Arg Ala
225                 230                 235                 240

Asn Pro Asp Phe Asn Val Arg Leu Leu Gly Trp Thr Asp Ser Thr Gly
                245                 250                 255

Pro Asp Ala Tyr Asn Leu Arg Leu Ser Gln Glu Arg Ala Asp Ala Val
            260                 265                 270

Lys Asn Phe Leu Val Lys Met Gly Ile Pro Ser Asn Arg Leu Phe Ala
            275                 280                 285

Lys Gly Met Gly Lys Ser Tyr Gln Tyr Asn Asn Ala Thr Lys Glu Gly
            290                 295                 300

Arg Tyr Met Asn Arg Arg Thr Glu Leu Val Phe Phe Asp
305                 310                 315

<210> SEQ ID NO 6
<211> LENGTH: 576
<212> TYPE: PRT
<213> ORGANISM: Artificial Sequence
<220> FEATURE:
<223> OTHER INFORMATION: Synthetic OMP2 "OMP2q"
<220> FEATURE:
<221> NAME/KEY: MISC_FEATURE
<222> LOCATION: (319)..(327)
<223> OTHER INFORMATION: Epitope
<220> FEATURE:
<221> NAME/KEY: MISC_FEATURE
<222> LOCATION: (349)..(357)
<223> OTHER INFORMATION: Epitope

<400> SEQUENCE: 6

Ser Ile Thr Thr Ser Thr Ile Asn Gln Gln His Ile Ala Tyr Thr Val
1               5                   10                  15

Thr Phe Thr Ser Pro Glu Asn Pro Asn Leu Ala Thr Glu Met Glu Thr
            20                  25                  30

His Ser Glu Leu Val Lys Leu Ala Asn Gln Ser Leu Asp Ser Lys Ile
        35                  40                  45

Gly Leu Asn Leu Arg Val Lys Glu Asp Ile Ser Thr Ala Gln Lys Ile
    50                  55                  60

Leu Asp Ser Asn Gly Tyr Tyr Ser Gly Ser Val Glu Gly Lys Ile Asp
65                  70                  75                  80

Trp Gln Thr Asn Pro Ile Ser Ile Gln Ile Gln Phe Lys Pro Asn Val
                85                  90                  95

Gln Tyr Lys Ile Asn Thr Ile His Ile Gln Tyr Leu Asp Ser Glu Leu
            100                 105                 110

Ala Tyr Leu Pro Leu Ser Leu Glu Glu Phe Asn Leu Ser Lys Gly Asn
        115                 120                 125

Pro Ala Leu Ala Val Asn Ile Leu Ser Ser Val Ser Ser Leu Met Gln
    130                 135                 140

Tyr Ile His Asn Asn Gly Tyr Pro Leu Ala Lys Ile Lys Lys Thr Gln
145                 150                 155                 160
```

```
Tyr Ile Ile Asn Arg Met Asp Tyr Thr Phe Asp Ile Asp Leu Val Ile
                165                 170                 175

Arg Gln Gly Pro Leu Leu His Met Gly Lys Val Gln Pro Gln His Asn
            180                 185                 190

Leu Asn Ile Ser Thr Ile Phe Leu Asn Lys Ile Ala Thr Trp Lys Glu
            195                 200                 205

Gly Arg Val Trp Asn Asn Ala Leu Leu Asp Ser Tyr Arg Thr Arg Leu
        210                 215                 220

Gln Gln Thr Gly Leu Phe Ser Ser Ile Thr Leu Asn Pro Arg Asn Gln
225                 230                 235                 240

Lys Glu Gln Asn Gly Asn Thr Ser Ile Glu Leu Val Ala Thr Glu Ala
                245                 250                 255

Pro Pro Arg Thr Ile Ser Gly Gly Leu Gln Tyr Ser Ser Asp Gln Gly
                260                 265                 270

Ile Gly Ala Arg Gly Thr Trp Glu His Arg Asn Val Phe Gly Asn Gly
                275                 280                 285

Glu Leu Phe Arg Ile Thr Ala Pro Ile Ser Arg Asp Asp Gln Lys Ile
        290                 295                 300

Met Ala Asn Phe Gln Lys Pro Ala Phe Gly Arg Pro Asn Gln Phe Ser
305                 310                 315                 320

Tyr Ala Thr Asp Leu Ser Tyr Lys Glu Asn Thr Lys Ser Tyr Lys Gln
                325                 330                 335

Gln Leu Ala Ser Ile Ala Leu Gly Ile Glu Arg Gln Phe Asn Arg Arg
                340                 345                 350

Trp Phe Gly Ser Ser Ser Leu Ser Val Asp Thr Gly Phe Met Asp Asp
        355                 360                 365

Arg Asp Ser Ile Lys Lys Ile Phe Thr Leu Phe Gly Ile Pro Leu Ser
370                 375                 380

Ile Thr Arg Asp Ser Ser Lys Asp Pro Leu Asn Pro Ile Gln Gly Thr
385                 390                 395                 400

Lys Ala Thr Leu Asn Val Thr Pro Tyr Ile Gly Lys Tyr Lys Lys Lys
                405                 410                 415

Ile Leu Thr Leu Arg Ser Arg Phe Asp Phe Ser Phe Tyr Ile Asp Val
                420                 425                 430

Leu Lys Thr Gly Lys Leu Ile Leu Ala Asn Lys Ile Ala Ile Gly Ser
                435                 440                 445

Phe Ser Phe Pro Tyr Trp Phe Thr Phe Pro Ala Ile Leu Arg Phe Tyr
450                 455                 460

Ala Gly Gly Gly Gly Ser Val Arg Gly Tyr Asp Tyr Gln Ser Leu Gly
465                 470                 475                 480

Pro Lys Asn Lys Tyr Gly Asp Ala Ile Gly Gly Leu Ser Phe Ser Thr
                485                 490                 495

Ile Ser Phe Glu Leu Arg Leu Lys Ile Thr Glu Ser Ile Gly Ile Val
                500                 505                 510

Pro Phe Ile Asp Gly Gly Asn Ile Tyr Glu Lys Lys Phe Pro Asp Phe
            515                 520                 525

Lys Lys Ser Ile Tyr Trp Gly Val Gly Leu Gly Leu Arg Tyr Tyr Thr
530                 535                 540

Ser Phe Ala Pro Ile Arg Leu Asp Ile Ala Thr Pro Leu Gln Asp Arg
545                 550                 555                 560

Ser His Asn Lys His Phe Gln Leu Tyr Ile Ser Ile Gly Gln Ala Phe
                565                 570                 575
```

```
<210> SEQ ID NO 7
<211> LENGTH: 4068
<212> TYPE: DNA
<213> ORGANISM: Artificial Sequence
<220> FEATURE:
<223> OTHER INFORMATION: Expression cassette (tandem SEQ ID NO: 1 + SEQ
      ID NO: 2 + SEQ ID NO: 3)
<220> FEATURE:
<221> NAME/KEY: promoter
<222> LOCATION: (6)..(22)
<223> OTHER INFORMATION: T7 promoter
<220> FEATURE:
<221> NAME/KEY: protein_bind
<222> LOCATION: (25)..(47)
<223> OTHER INFORMATION: LAC operator
<220> FEATURE:
<221> NAME/KEY: RBS
<222> LOCATION: (80)..(85)
<220> FEATURE:
<221> NAME/KEY: terminator
<222> LOCATION: (849)..(895)
<223> OTHER INFORMATION: T7 terminator
<220> FEATURE:
<221> NAME/KEY: promoter
<222> LOCATION: (916)..(932)
<223> OTHER INFORMATION: T7 promoter
<220> FEATURE:
<221> NAME/KEY: protein_bind
<222> LOCATION: (935)..(957)
<223> OTHER INFORMATION: LAC operator
<220> FEATURE:
<221> NAME/KEY: RBS
<222> LOCATION: (990)..(995)
<220> FEATURE:
<221> NAME/KEY: terminator
<222> LOCATION: (2044)..(2090)
<223> OTHER INFORMATION: T7 terminator
<220> FEATURE:
<221> NAME/KEY: promoter
<222> LOCATION: (2111)..(2127)
<223> OTHER INFORMATION: T7 promoter
<220> FEATURE:
<221> NAME/KEY: protein_bind
<222> LOCATION: (2130)..(2152)
<223> OTHER INFORMATION: LAC operator
<220> FEATURE:
<221> NAME/KEY: RBS
<222> LOCATION: (2185)..(2190)
<220> FEATURE:
<221> NAME/KEY: terminator
<222> LOCATION: (4016)..(4062)
<223> OTHER INFORMATION: T7 terminator

<400> SEQUENCE: 7
gaaattaata cgactcacta tagggaatt gtgagcggat aacaattccc ctctagaaat      60
aattttgttt aactttaaga aggagatata catatgcaga caggacttta catcgcgccg    120
aaatttattt ggggtttcgc gccggtcgat atcaaaacca cggtacgat tggcattgtc     180 aatgtacaga ccatctccga tagcgtctct cataaaaaaa cagaatctct tcccggtttc   240
tcttatgcca ctgatcttag ttacaatcac atgtttcaaa ccccgatccg caccgagctc   300
gaattttcct tctttaaaaa aatggatatt aaacacaatg acaaaaaaac tgatattact   360
ctgggcgctt tacttgttaa cggctatttt gatattaaaa ccgattcacc gttcacgcct   420
tacattggag taggtttagg aattgcagga gttaaaacaa aaagcaacgc tattattgat   480
tcacttggat acgacatcaa agtaaaactg gacgataaaa caaaaaaaaa ttttgcatgg   540
atggcaacag taggcacctc gtatgaaatt ccgaaacat ttgcactgga tctgggctac    600 cgcttttgcag gcttcggtaa aggtgagact aaatcctgga caaattctc tttcccttac   660 tggtttacct tcggccccgt taccgctacc gccaacgcta acaatttaa ccttaacacc    720
```

```
ttattaatgc atcagattat cttatccgcc cgccttacat ttagcggcgg aggcggccac    780
caccaccacc accactgaca aagcccgaaa ggaagctgag ttggctgctg ccaccgctga    840
gcaataacta gcataacccc ttggggcctc taaacgggtc ttgaggggtt ttttggtcga    900
catcggatcc gaaattaata cgactcacta gggggaatt gtgagcggat aacaattccc    960
ctctagaaat aattttgttt aactttaaga aggagatata catatggccg aagtgacagc   1020
ctcatgtaca aaacgcgtcg aaagttacaa ttatcttgtt gactactctg gatttagtta   1080
tgcgaccgat ctctcttatc gtgaaccgaa aattgaatta gcaaaagaag cgattttaaa   1140
aattaatgcc gcaatgccta agatgtcata ccaaggtgga ttatatacct ttgcgcctta   1200
ctctgtaatc atcccacaag gatcttggaa ttcatgcttt agttttccgt actggtttac   1260
ctttaaaagc gacctcgaaa tctttggacg tttgaccccca atgggcgatg gtatcaaaat   1320
gcatgaaaca gttatcaacc aaatgccgcc tcaagccgcc gtaatcctgt taaccgatgg   1380
ccataacaat ctcggaatga atccagttga agaagtaaaa tcaatctatc agaccaatcc   1440
aaatgtgtgt tttcatgttg catccttttgc cgatgacgcg gaaggtaaag cgattattga   1500
ccaaattgtt gcgttgaact caggtagtgt actcgtggat gggcttcaac tcttgcaaaa   1560
ccccgcagtt tgtcaggaat cgttaacag cgtgttttgc caaggccaga tccttgtaac   1620
tgaagaagtc gtcgtgctgc gtggtgtgaa ctttgctttt gattcgtttg ccctggatga   1680
tacggctaaa gctatcagtg aagaaacagt ccgcttgatt cgtgcgaacc ctgatttaa    1740 tgttcgcctg ctgggctgga ccgactcgac aggcccggat gcatataatc tccgtctcag   1800
ccaagaacgc gccgatgccg ttaaaaactt tttagtaaaa atgggtattc cgtctaaccg   1860 tctgttttgca aaaggtatgg gtaagtctta tcaatacaat aatgccacta agaaggccg    1920 ctatatgaat cgccgtaccg aattggtgtt ttttgatagc ggcggaggcg gccaccacca   1980
ccaccaccac tgacaaagcc cgaaaggaag ctgagttggc tgctgccacc gctgagcaat   2040
aactagcata accccttggg gcctctaaac gggtcttgag ggttttttg gtcgacatcg     2100 gatccgaaat taatacgact cactataggg gaattgtgag cggataacaa ttcccctcta   2160
gaaataattt tgtttaactt taagaaggag atatacatat gtctatcacc acaagtacca   2220
ttaatcaaca gcatatcgcc tacaccgtaa ctttcacctc ccctgaaaat ccgaatttag   2280
ccacggaaat ggaaacgcat agtgagcttg tcaaattagc caaccaaagc ctggattcaa   2340
aaatcggttt gaacctgcgt gtaaaagaag acatctccac cgcacaaaaa atcctggaca   2400
gtaacggata ttatagcggt tcagttgagg gtaaaatcga ttggcagacc aaccccatca   2460
gtattcagat tcaatttaaa ccaaacgtac aatacaaaat taacaccatt catatccaat   2520
accttgactc ggaactggcg tatttaccgc tcagccttga agagtttaac ctgtctaagg   2580
gcaatcccgc actggccgtg aatatttaa gctcggtgag ctctttaatg caatatattc   2640
acaataatgg ttaccccctc gctaaaatca aaaagacgca atatattatc aatcgtatgg   2700 attataccctt tgacatcgat ctggtgatcc gtcaaggtcc cttactgcac atgggcaaag   2760
tacaaccgca gcataacctg aacatttcca ccatcttctt aaataaaatt gcaacctgga   2820
aagaaggacg cgtatggaat aatgcacttc tggactcata tcgcacccgt ttacagcaga   2880
ccggcctgtt ttcttccatt actctgaacc cgcgcaatca aaaagaacag aacgggaaca   2940
cctctatcga attagtagca accgaagctc cgccacgtac gatttcaggg gggctgcaat   3000
attccagtga tcagggtatc ggcgcccgcg gcacctggga acatcgcaac gttttttggca   3060
```

```
acggcgaatt attccgtatc accgccccaa tttcccgcga cgaccagaaa attatggcca    3120
actttcagaa accagcattt ggacgcccaa atcagttctc ttacgccacc gacctctcct    3180
acaaagagaa taccaagtcc tacaaacagc aactggcaag catcgcgtta ggtattgaac    3240
gtcagtttaa ccgccgctgg ttcggtagct cttcgttaag tgttgataca ggctttatgg    3300
atgaccgcga ctcaatcaaa aaaatctttta cgctctttgg tattccgctg tcaattacac    3360
gcgattcgtc aaaggaccca ttaaacccga tccagggac caaagcaaca ttaaatgtca    3420
cgccctatat tggtaaatac aaaaaaaaaa tcctgactct gcgcagtcgt ttcgattttt    3480
ctttctatat tgacgtactg aaaaccggta aactgattct ggcgaataaa atcgcgattg    3540
gctcgttctc ttttccctat tggtttacat tccctgcaat tttacgtttt tacgccggtg    3600
gcggcggatc tgtacgcggc tacgattatc aaagcctggg cccgaagaat aaatacggcg    3660
atgccattgg cggcctgtct ttctcaacca tctccttcga actgcgtctt aaaatcactg    3720
agtccatcgg gatcgtccct tttattgatg gaggtaacat ttatgaaaaa aaatttcccg    3780
actttaaaaa gagcatttat tggggcgttg gccttggcct ccgttattat acaagctttg    3840
caccaatccg tcttgatatc gccaccccgt tgcaggaccg ctcccataac aaacatttcc    3900
aactgtacat ctccattgga caggctttta gcggcggagg cggccaccac caccaccacc    3960
actgacaaag cccgaaagga agctgagttg gctgctgcca ccgctgagca ataactagca    4020 taacccctg gggcctctaa acgggtcttg aggggttttt tgctcgag    4068
```

<210> SEQ ID NO 8
<211> LENGTH: 9
<212> TYPE: PRT
<213> ORGANISM: Artificial Sequence
<220> FEATURE:
<223> OTHER INFORMATION: Epitope

<400> SEQUENCE: 8

Phe Ser Tyr Ala Thr Asp Leu Ser Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: Epitope

<400> SEQUENCE: 9

Phe Ser Phe Pro Tyr Trp Phe Thr Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Epitope

<400> SEQUENCE: 10

Lys Gln Phe Asn Leu Asn Thr Leu Leu
1               5